Figure 1:
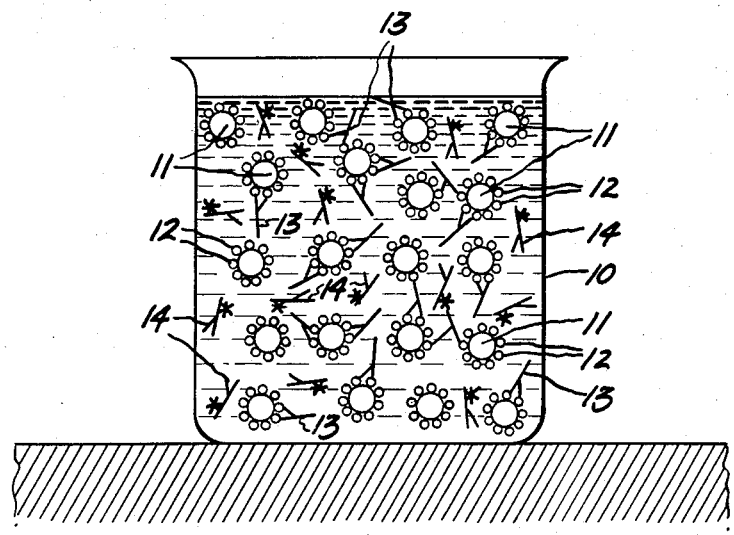

United States Patent [19]

Giaever et al.

[11] Patent Number: 4,634,681

[45] Date of Patent: Jan. 6, 1987

[54] DIAGNOSTIC METHOD OF DETERMINING THE PRESENCE OR ABSENCE OF SELECT PROTEINS IN A LIQUID SAMPLE

[75] Inventors: Ivar Giaever, Schenectady; Charles R. Keese, Schoharie, both of N.Y.

[73] Assignee: General Electric Company, Schenectady, N.Y.

[21] Appl. No.: 665,902

[22] Filed: Oct. 29, 1984

[51] Int. Cl.$^4$ .......................................... G01N 33/543
[52] U.S. Cl. ............................ 436/518; 436/528; 436/800; 436/804; 436/829
[58] Field of Search .................... 428/402.2; 264/4.1; 436/518, 528, 800, 804, 829

[56] References Cited

U.S. PATENT DOCUMENTS

| | | | |
|---|---|---|---|
| 3,406,119 | 10/1968 | Kosar et al. | 264/4.1 |
| 3,970,518 | 7/1976 | Giaever | 195/1.5 |
| 4,018,886 | 4/1977 | Giaever | 424/12 |
| 4,041,146 | 8/1977 | Giaever | 424/1 |
| 4,308,165 | 12/1981 | Vassiliades et al. | 264/4.1 |

FOREIGN PATENT DOCUMENTS 0087036  5/1984  Japan ................................ 264/4.1

Primary Examiner—Christine M. Nucker
Assistant Examiner—Stephen C. Wieder
Attorney, Agent, or Firm—Francis T. Coppa; James C. Davis, Jr.; James Magee, Jr.

[57] ABSTRACT

An emulsion (in which an aqueous medium contains small liquid droplets coated with a protein that will interact specifically with a select protein) is mixed with a liquid sample, time is allowed for interaction to occur and the mixture is then exposed to a tagged antibody specific to the select protein. After an appropriate hold time the emulsion is broken and the protein that previously covered the disperse droplets becomes concentrated at the surface. The surface is checked for the presence of the tagged antibodies to establish the presence of absence of the select protein.

14 Claims, 2 Drawing Figures

DIAGNOSTIC METHOD OF DETERMINING THE PRESENCE OR ABSENCE OF SELECT PROTEINS IN A LIQUID SAMPLE

BACKGROUND OF THE INVENTION

This invention relates to the detection of proteins by the utilization of the phenomenon by which such proteins interact specifically either immunologically or non-immunologically.

The preparation and use of protein-coated droplets dispersed in a tissue culture medium for growing cells is described and claimed in the U.S. patent application Ser. No. 443,311—Giaever and Keese, filed Nov. 23, 1982. This application is incorporated by reference.

The use of small magnetic particles coated with a protein that will interact specifically with a select protein in order to separate such select protein from a solution is disclosed in U.S. Pat. No. 4,018,886—Giaever. Also, the use of small magnetic particles coated with an antibody layer for sorting out and separating select viruses, bacteria and other cells from multi-cell, bacteria or virus populations is disclosed in U.S. Pat. No. 3,970,518—Giaever.

The use of inert molecules as "spacers" for molecules of interest is described in pending U.S. patent application Ser. No. 358,219—Giaever, filed Mar. 15, 1982 and assigned to the assignee of the instant application.

The preparation of tagged biological particles is described in U.S. Pat. No. 4,041,146—Giaever.

Fluorescent tagging is the preferred mode of tagging. The procedure for fluorescent tagging as well as radioactive tagging are generally understood by those skilled in the art. Suitable methods for fluorescent tagging of an anchored layer of biological particles are thoroughly described in the aforementioned Handbook of Experimental Immunology in Chapter 18 "Immunofluorescence" by G. D. Johnson and E. J. Holborow.

Suitable methods for the radioactive tagging of biological particles are described in Principles of Competitive Protein-Binding Assays [Ed. W. D. Odell & W. H. Daughaday, Philadelphia: Lippincott (1971)] in chapter X "Radioiodination of Peptide Hormones: Procedure and Problems" by F. C. Greenwood pp. 288–296. Another reference work which describes suitable radioactive tagging methods is in Radioimmunoassay Methods [Ed. K. E. Kirkham & W. M. Hunter. Churchill: Livingstone (1971)] "The Preparation and Assessment of Iodinated Antigens" by W. M. Hunter pp. 3–23 and "The Immuradiometric Assay" by G. M. Addison and C. N. Hales pp. 447–461.

These teachings are incorporated by reference as they are representative of the methods useful for tagging biological particles employed in the practice of the invention disclosed herein.

U.S. patent application Ser. No. 665,867—Giaever and Keese, filed Oct. 29, 1984, discloses and claims an invention in which small liquid droplets, coated with a protein that will interact specifically with a select protein, are contacted with a liquid sample to determine the presence or absence of the select protein therein depending upon whether the droplets agglutinate. This application is assigned to the assignee of this inventon and is incorporated by reference.

A common test for pregnancy involves coating small polystyrene latex spheres with the hormone, human chorionic gonadotropin (HCG). When a woman becomes pregnant, the level of HCG in the urine increases significantly. This is an indirect test in which a quantity (as determined by titer by an established procedure) of antibodies to HCG is added to a sample of female urine and is allowed to incubate for from about 5 to about 10 minutes therein. Next, HCG-covered latex spheres are mixed with the urine and the mix is allowed to incubate for from about 5 to about 10 minutes. If agglutination of the spheres takes place, the urine does not contain HCG to the level establishing a pregnant condition; if the spheres remain in single suspension, HCG was present beyond that level.

These tests can be generalized to detect any antigen or antibody. The fact of agglutination preferably should be visible to the ordinary observer.

DESCRIPTION OF THE INVENTION

An emulsion is, typically, a heterogeneous system with at least one immiscible liquid dispersed in another in the form of droplets. The phase providing the droplets is the dispersed, or internal, phase while the phase providing the matrix for the dispersed phase is the continuous, or external phase.

According to this invention, a large number of small droplets of a first liquid are dispersed in a second liquid in the nature of an emulsion. The second liquid is an aqueous medium and the first liquid is relatively immiscible with the second liquid. The resulting liquid droplets receive a coating of a specific protein (e.g., a coating of a particular antibody, that will interact specifically with some select protein (e.g. a select antigen).

The initial protein coating can be provided in the aqueous medium used to prepared the emulsion or can be added after the emulsion has been prepared. Preferably the concentration of this protein is known. A contact period between the protein material and the liquid droplets of less than one hour is usually sufficient, when protein concentrations upwards of 10 micrograms/ml. are employed.

In those instance in which the desired protein coating does not adhere to the liquid droplets unaided, the necessary attachment should be obtained chemically by introducing a small amount of a fluorinated polar compound (e.g., pentafluorobenzoyl chloride) to the first (i.e., the droplet) liquid.

Having coated the liquid droplets with the requisite specific protein, the emulsion is then gently centrifuged segregate the droplets from the bulk of the aqueous medium. The supernatant aqueous medium is then removed (e.g., by decanting). Next, the coated droplets are washed at least once with an aqueous solution of a non-specific protein (about 100 micrograms of the non-specific protein per milliliter of 0.15 molar sodium chloride solution). The protein-coated droplets are then re-suspended in dilute (i.e., about 0.15 molar NaCl) saline solution at pH 7.5. It may be necessary to use a buffer, such as 0.01 molar trishydroxymethylaminomethane. These protein-coated liquid droplets present in a concentration of from about $10^6$ to about $10^{10}$ droplets/cc are now suitable for contact with a liquid sample to be tested for the presence or absence of the specific protein. The liquid sample is normally a body fluid, such as blood or urine.

Utilization of the protein-coated liquid droplets may be effectuated either by adding the sample of body fluid to the liquid volume containing the protein-coated liquid droplets or, vice versa. Once either addition has been made, the volume of liquid is subjected to gentle rocking action for about 15 minutes to increase the number of contacts between the protein-coated droplets and the body fluid content. The volume is then inspected for the presence of agglutination, which would indicate that the specific biological reaction has occurred.

The procedure can be modified to increase the sensitivity of the test by making the agglutination more effective. This can be accomplished by coating the liquid droplets with a mixture of proteins (one of which is the initial, or specific, protein and the rest of the protein content is non-specific to the select protein) such that the number of protein molecules available on the droplets to interact specifically with the select protein is a very small percentage of the mixture. With this arrangement, whereas approximately $10^4$ molecules will locate themselves over the surface of a 1 micrometer diameter liquid sphere, when utilizing the protein mixture, on the order of a few hundred of the specific protein molecules will distribute themselves at locations over the sphere by and large separated from each other by large numbers of the non-specific protein molecules. In this way, the interaction of the select protein molecules, if present, will, at least statistically, occur such that each select protein molecule will initially interact with one single specific protein molecule per liquid droplet leaving one interactive site available for interconnection with an accommodating binding site on another liquid droplet thereby increasing the driving force for agglutination.

This modified procedure is of particular use, when the concentration of select protein in the sample is very high or quite low. Also, the ability to use smaller amounts of the specific protein becomes important when the specific protein is expensive.

In the preferred embodiment of this invention, if agglutination in the mixture is not evident to the viewer at this point, it is conceivable that the select protein is present, but in very low concentration. Preferably, to make this determination the concentrating, decanting and washing steps are repeated to remove unreacted sample. Thereafter, a quantity of tagged (e.g. with a fluorescent molecule or a radioactive moiety) biological particles (i.e. tagged molecules of a third protein) that will interact specifically with the select protein, but not with the specific protein initially applied to the droplets, is added to the emulsion/mixture.

After a suitable residence time the concentrating, decanting and washing steps are repeated. Next, the emulsion is broken (i.e. demulsification). This breaking of the emulsion is readily accomplished by spinning or centrifuging the system for larger droplets and more severe mechanical action for very small droplets whereupon the disperse phase agglomerates and the now insoluble denatured protein molecules (i.e. specific protein) previously coating the droplets of disperse phase rise to the interface between the two immiscible continuous phases accompanied by whatever molecules, if present, that will have interacted therewith. Thus, molecules of the select protein, if present, will have affixed themselves to molecules of the specific proteins and, in turn, tagged third protein molecules that will have interacted with select protein molecules will be present in the now-concentrated collection of proteins. By examining this thin layer for evidence of the tagged molecules, it can be determined whether the select protein is present, albeit in small concentration.

Normally the third protein molecules will be antibodies to the select protein produced in living systems. Because a higher concentration of these antibodies will be more readily available, the time interval of exposure thereto is generally shorter than the contact time following the mixing of the sample with the emulsion. Typical incubation times will be one hour for the first incubation and 15 minutes for the second.

Both fluorocarbon and silicone oils have been found suitable as liquid droplets as substrates for protein coatings. The fluorocarbons are characterized by lack of toxicity, inertness, high density (about 1.5 to 1.9 $gm/cm^3$), immiscibility with water, low solubility for most other materials, thermal and chemical stability, low viscosity, transparency and hydrophobicity. The fluorocarbon oils that have been used are the FC-43, FC-70, FC-75, FC-104 marketed by the 3M Company, St. Paul, Minn. and alumina-treated FC-43. In addition, work has been done with silicone oil (General Electric Co. SF1265).

Droplets having an average particle diameter of about 0.1 micrometers to 5 micrometers may be used in the practice of this invention. The typical average droplet diameter used being about one micrometer.

As a variant of the aforementioned embodiments the select protein molecules and/or the non-specific protein molecules employed to coat the droplets may be supplied with fluorescent or radioactive tag moieties to enhance detection of agglomeration.

There are several advantages to using liquid droplets in place of solid spheres. First, liquid particles can deform and allow for a greater area of contact between adjacent particles in an agglutinated mass. The availability of this property means that the liquid shear forces that can be withstood by the agglutinated mass is high. Second, the oil emulsion is substantially uncharged and appears to be usable over a wide range of pH values compared to latex particles which must be used at pH 8. Third, experience with the emulsion to date has shown that it works very well in whole serum, while latex particles do not. Fourth, the density of the liquid droplets can be adjusted within wide limits and can, if desired, be made to match the density of water. Finally, the emulsion can be broken to concentrate the tagged protein making tag detection easier.

BRIEF DESCRIPTION OF THE DRAWING

The subject matter of the instant invention for which protection is sought is presented as claims at the conclusion of the written description of the invention set forth herein. The description sets forth the manner and process of making and using the invention including the best mode contemplated therefor, and the accompanying drawing forms part of the description for schematically illustrating the practice of the invention.

The view shown in FIG. 1 shows apparatus for contacting the emulsion containing the protein-coated droplets according to this invention after having been mixed with a sample liquid (suspected for containing the select protein) washed and the tagged protein having just been added, and FIG. 2 shows the system of FIG. 1 after breaking of the emulsion resulting in concentration of the denatured protein being examined for the identifying tags.

MANNER AND PROCESS OF MAKING AND USING THE INVENTION

The apparatus and materials disclosed herein are merely exemplary and, after an understanding of the method of this invention, other embodiments may be readily devised.

The apparatus and materials disclosed herein are merely exemplary and, after an understanding of the method of this invention, other embodiments may be readily devised.

Having identified the particular select protein (e.g., antibody or antigen) to be detected, a small amount of fluorocarbon oil is placed in a container (e.g. a beaker or test tube) together with a much larger quantity of an aqueous phase. Preferably the protein with which the liquid droplets are to be coated is introduced prior to emulsification. In such a case, typically about 20 milligrams of the specific protein in 3.5 ml. of saline (0.15M NaCl; no buffer) is added to 100 microliters of the disperse phase (the oil). This would be the equivalent of about 1 to about 5 micrograms of protein per square centimeter of droplet surface area.

This liquid system is subjected to agitation (e.g., mechanical stirring, sonication) sufficient to bring about emulsification. A useful device for accomplishing this effect is the Polytron ® (Brinkman Instruments, Westbury, N.Y.), which simultaneously provides the actions of sonication and mechanical agitation. Operation of this device at a setting of 7 will yield droplets of the oil in the useful range of about 0.1 to about 5.0 micrometers in diameter. Depending upon the nature of the specific protein, an agitation period of about 1 to 4 minutes with this device will yield droplets having an average diameter of about 1 micrometers.

If the specific protein addition is made after the emulsification, the coating process may be less effective (i.e., agglutination may occur). Thus, for example, it has been found that droplet coating after emulsification with bovine serum albumin was successful, while the same sequence using IgG immunoglobulin was not successible.

Whether pre-emulsification or post-emulsification addition of the specific protein is employed, the protein should be added in excess of the amount theoretically required to coat the droplets in order to insure very rapid coating of the droplets.

As noted hereinabove, if the protein was not added prior to the emulsifying step, it would be added at this point and mixed with the emulsion by gentle agitation. After a sufficiently long contact period, the emulsion is cleansed to remove the excess specific protein.

Cleansing of the protein-coated droplets is accomplished by concentrating the protein-coated droplets as by gentle centrifugation, decanting the supernatent and then washing with a solution of non-specific protein. The concentrating, decanting and washing may be repeated as needed. After the washing step, the clean select protein-coated droplets are re-suspended in 0.15 molar NaCl with a buffer, if needed to provide a pH of about 7.5. Care is to be taken, of course, in the cleansing operation not to break the emulsion.

The washing with non-specific protein is also important in that it helps to keep the protein-coated droplets stable.

Next, a volume of the liquid sample of body fluid to be assayed for specific protein content is brought into contact with (i.e., is added to and mixed with) the emulsion in which the protein-coated liquid droplets form the disperse phase. The period of mixing may vary from less than 5 minutes to as much as 30 minutes (depending upon concentration).

Next, no agglutination being evident visually, a concentration of the molecules of the tagged (e.g. fluorescent tagged) third protein is added and mixed with the emulsion.

At this point, the distribution of the material content of beaker 10 schematically illustrated in FIG. 1 will prevail i.e., before interaction has occurred between the select protein molecules present (attached to the initial protein layer) and the tagged molecules of the third protein. As shown, liquid droplets 11 are provided with a monomolecular coating of specific protein (e.g., an antigen) 12 which has interacted specifically with the select protein for which the assay is being run. Molecules of the tagged (identified by asterisks) third protein that have been added and mixed with the emulsion are designated by numerals 14.

Figure 2:
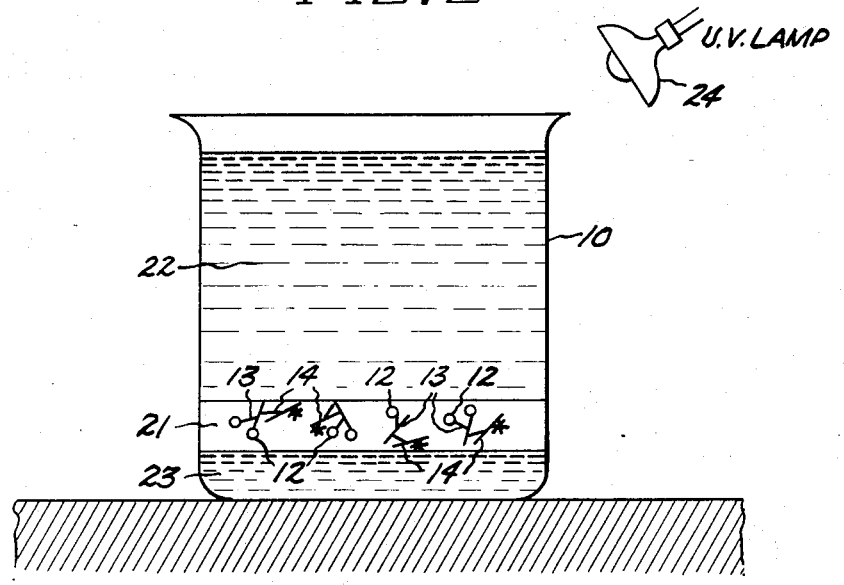

The system shown in FIG. 2 prevails after (1) sufficient time has elapsed for the tagged protein molecules 14 to interact with select protein (e.g. antibody) molecules 13 (which in turn are bound to protein coating molecules 12), (2) thorough washing of the emulsion to remove any protein not affixed directly or indirectly to droplets 11 and (3) breaking of the emulsion. In order to simplify the drawing only a few of the combinations of attached molecules 12, 13, 14 present in thin, solid protein layer 21 (shown greatly exaggerated in thickness) are shown. Layer 21 is supported on more dense layer 23 of fluorocarbon liquid (from the broken droplets 11) at the interface with aqueous layer 22.

Assuming the use of fluorescent tags, it is merely necessary to expose the system to UV-light from lamp 24. If brighter luminescence emanates from the surface layer 21. this indicates the presence therein of a concentration of fluorescent moieties. In the test described herein, therefore, this will establish the presence of the low concentration of the select protein in the liquid sample. It is expected that the sensitivity of this process will be more sensitive than the conventional radioimmune assay.

What is claimed is:

1. The diagnostic method for determining the presence or absence of select protein in a liquid sample comprising the steps of:
    (a) preparing an emulison in which a first liquid is dispersed as a large number of small protein-coated liquid droplets in a second liquid, said second liquid being an aqueous medium, said first liquid being relatively immiscible with said second liquid, and the protein coating said droplets including molecules of a protein having the property of interacting specifically with said select protein;
    (b) contacting the protein-coated droplets in said emulsion with a solution containing proteinaceous material for a suitable period of inoculation;
    (c) adding tagged protein molecules to the emulsion, said tagged protein having the property of interacting specifically with said select protein, but not with the protein coating said droplets;
    (d) removing tagged protein molecules not affixed directly or indirectly to said droplets from the emulsion;
    (e) breaking said emulsion to produce a continuous phase of said first liquid spaced from said second liquid by a thin interfacial layer, and
    (f) determining the presence or absence of tags in said interfacial layer.

2. The method of claim 1 wherein the first liquid is significantly greater in density than the second liquid.

3. The method of claim 1 wherein the proteinaceous material is contained in serum.

4. The method of claim 1 wherein the diameters of the droplets are in the range of from about 0.1 micrometers to about 5 micrometers.

5. The method of claim 1 wherein the droplet density is in the range of from about $10^6$ to about $10^{10}$ droplets per cubic centimeter of emulsion.

6. The method of claim 1 wherein the second liquid is a fluorocarbon.

7. The method of claim 1 wherein the second liquid is silicone oil.

8. The method of claim 1 wherein the protein coating the droplets comprises antibody moleclues.

9. The method of claim 1 wherein the protein coating the droplets comprises antigen molecules.

10. The method of claim 1 wherein the tagged protein molecules are tagged with fluorescent molecules.

11. The method of claim 1 wherein the tagged protein molecules are tagged with radioactive moieties.

12. The method of claim 1 wherein the protein coating consists of a mixture of molecules of protein able to interact specifically and molecules of non-specific protein.

13. The method of claim 12 wherein the ratio of the molecules of protein able to interact specifically to the molecules of non-specific protein is in the range of from about 1:30 to about 1:1000.

14. The method of claim 1 wherein after step (b) the proteinaceous material in solution is removed from the emulsion before proceeding to step (c).

* * * * *